United States Patent
Russel

(10) Patent No.: US 6,824,830 B1
(45) Date of Patent: Nov. 30, 2004

(54) WOOD TREATMENT

(75) Inventor: Philip Eric Russel, Great Shelford (GB)

(73) Assignee: Aventis Cropscience GmbH (DE)

( * ) Notice: Subject to any disclaimer, the term of this patent is extended or adjusted under 35 U.S.C. 154(b) by 0 days.

(21) Appl. No.: 10/111,351

(22) PCT Filed: Oct. 17, 2000

(86) PCT No.: PCT/EP00/10648

§ 371 (c)(1),
(2), (4) Date: Aug. 13, 2002

(87) PCT Pub. No.: WO01/28331

PCT Pub. Date: Apr. 26, 2001

(30) Foreign Application Priority Data

Oct. 20, 1999 (GB) .............................. 9924692

(51) Int. Cl.$^7$ ............................................... B05D 7/06
(52) U.S. Cl. ...................................................... 427/384
(58) Field of Search ......................................... 427/384

(56) References Cited

U.S. PATENT DOCUMENTS

| 5,885,934 A | 3/1999 | Heistracher et al. ........ 504/169 |
| 5,977,149 A | 11/1999 | Brown et al. ................ 514/362 |

FOREIGN PATENT DOCUMENTS

| AU | 708842 | 4/1997 |
| DE | 19724200 | 12/1998 |
| DE | 19731153 | 1/1999 |
| DE | 19732846 | 2/1999 |
| EP | 0 332 387 | 9/1989 |
| HU | P8901034 | 12/1990 |
| HU | P9800770 | 7/1998 |
| HU | P9901177 | 7/1999 |
| WO | 96/36615 | 11/1996 |
| WO | WO 96 / 36633 | * 11/1996 |
| WO | 97/00612 | 1/1997 |
| WO | WO 98 / 05652 | * 2/1998 |
| WO | WO 98 / 23156 | * 6/1998 |
| WO | WO 99 / 11129 | * 3/1999 |
| WO | WO 99 / 28305 | * 6/1999 |
| WO | 99/46246 | 9/1999 |
| WO | 00/76317 | 12/2000 |

* cited by examiner

Primary Examiner—Erma Cameron
(74) Attorney, Agent, or Firm—Ostrolenk, Faber, Gerb & Soffen, LLP

(57) ABSTRACT

A method is disclosed for reducing damage to wood from wood damaging fungi comprising applying to said wood a fungicidal composition comprising a fungus-controlling amount of at least one compound of the formula:

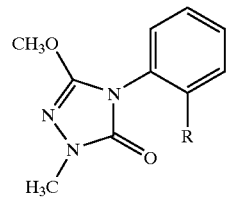

wherein:
R is a member selected from the group consisting of moieties of the structures:

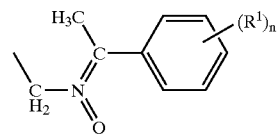

and

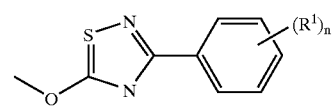

wherein:
each $R^1$ is independently selected from the group consisting of $C_1$–$C_4$ alkyl, $C_1$–$C_4$ alkoxy, trifluoromethyl, and halogen; and
n is 0 to 3.

12 Claims, No Drawings

WOOD TREATMENT

This application is the U.S. National Phase of International Application Number PCT/EP00/10648, filed October 17, 2000.

FIELD OF THE INVENTION

This invention relates to wood preservation.

In WO 96/36615 and 97/00612, are disclosed various cyclicureas as fungicides for combating plants diseases.

We have now found that a specific group of compounds are very effective in controlling wood damaging fungi and particularly basidiomycete fungi, which cause rot, as well as sapstain fungi which spoil the appearance of the wood.

The invention thus provides the use for combating wood damaging fungi of compounds of formula I

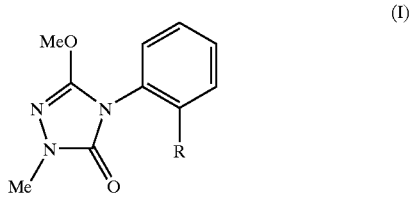

where R is
a)

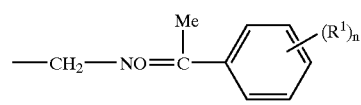

or
b)

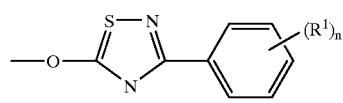

where each $R^1$, which may be the same or different, is $C_{1-4}$-alkyl, $C_{1-4}$-alkoxy, trifluoromethyl or halogen and n is 0 to 3.

Examples of fungi that can be controlled using the compounds of formula I include *Coriolus versicolor, Poria placenta, Lentinus lepideus, Trametes versicolor, Serpula lacrymans, Coniophora puteana* and *Gloeophyllum trabeum*.

In general the wood rotting fungi appear as a complex of two or more of these species.

We have also found that the compound of formula I is particularly effective when used in combination with other wood fungicides, such as fluquinconazole, tebuconazole, dichlone, carbendazim, prochloraz, sipconazole and cyproconazole.

The compound of formula I can be applied in a suitable, usually liquid formulation usually containing surfactants and other conventional additives and usually after dilution with water. The concentration may vary over a wide range, e.g. from 0.001 to 10%, preferably from 0.1 to 1%, by weight.

The invention is illustrated In the following examples.

EXAMPLE 1

In Vitro Test of Activity Against Wood Destroying Fungi 10 cm feather edge boards of fresh cut pine were cut into 20 cm lengths. Each replicate consisted of 6 boards stacked alernately to form a block 6 boards high. 3 replicates were used per treatment.

Each replicate was treated separately but with the same treatment solution of a compound to be tested. The complete bundle of 6 boards was immersed in the test solution with a 1 cm longitudinal strip being kept clear. Boards were separated slightly to allow free movement of the treatment solution between them. Treatment time was approx. 10 seconds after which the boards were removed from the treatment solution, excess liquid allowed to drain off and the boards put in a polythene bag. This bag had a small hole in the underside to allow excess moisture to drain away, while allowing a high humidity to be maintained.

Bagged boards were kept in a glasshouse at 18° C. with natural daylight. Bundles were kept as a single layer and not stacked. Bundles were turned periodically to ensure as consistent a moisture content within the bundle as possible.

Assessment was made 5 weeks after treatment. For each replicate, the adjacent faces of neighbouring boards were visually assessed for % infection by sapstain, % of board surface covered by basidiomycete colonisation, and % surface colonised by sooty moulds. As there were 6 boards in a bundle, this gave 5 readings per replicate. % control values were calculated based on infection levels on untreated boards.

The treatment consisted of 10 EC of compound A (Example 59 of WO 9636615), diluted to the desired concentration.

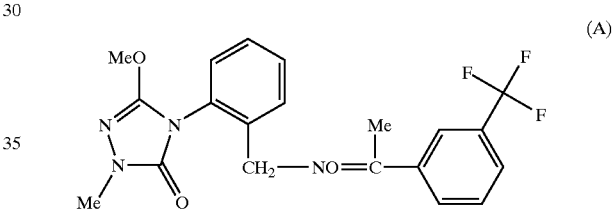

For comparison a commercial product Evotek (a 23% suspoemulsion of prochloraz and carbendazim) was used.

The results are as follows.

|  |  | % control of | | |
| --- | --- | --- | --- | --- |
| Treatment | Rate | Sapstain | Basidiomycetes | Sooty moulds |
| Compound A | 2% | 100 | 100 | 98 |
|  | 1% | 93 | 97 | 93 |
|  | 0.50% | 93 | 96 | 65 |
| Evotek | 2% | 100 | 0 | 97 |
|  | 1% | 99 | 0 | 99 |
|  | 0.50% | 98 | 0 | 100 |

It will be seen that the compound gives excellent control of sapstain and sooty mould, comparable with Evotek, but it also controls Basidiomycetes unlike Evotek. It is unusual to observe such activity against the complete range of wood pathogenic fungi.

EXAMPLE 2

In Vitro Test of Activity Against Wood Destroying Fungi

Compound A was incorporated into malt agar at various rates and the agar placed into Petri dishes. Into the centre of each plate was implanted a 4 mm plug of the mycelium of a wood rotting fungus. The plates were kept at 20° C. in a darkened room for 7 days when the control of the fungus by Compound A was assessed. The results are shown below.

| | % Control based on colony diameter | | | |
|---|---|---|---|---|
| Rate ppm | Coniophora puteana | Coriolus vesicolor | Gloeophyllum trabeum | Poria placenta |
| 100 | 100 | 100.0 | 100.0 | 100 |
| 25 | 100 | 93 | 92 | 93 |
| 10 | 100 | 76 | 56 | 70 |
| 1 | 100 | 42 | 38 | 54 |

What is claimed is:

1. A method of reducing damage to wood from wood damaging fungi comprising applying to said wood a fungicidal composition comprising a fungus-controlling amount of at least one compound of the formula:

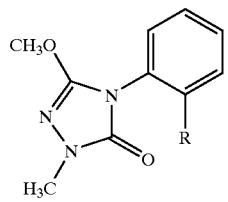

wherein:
R is a member selected from the group consisting of moieties of the structures:

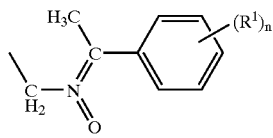

and

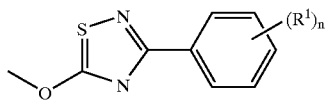

wherein:
each $R^1$ is independently selected from the group consisting of $C_1$–$C_4$ alkyl, $C_1$–$C_4$ alkoxy, trifluoromethyl, and halogen; and
n is 0 to 3;
wherein the fungicidal composition is applied to the wood as a solution comprising the compound in a concentration in the range of from 0.1 to 1% by weight.

2. The method of claim 1 wherein the controlled fungus is at least one member selected from the group consisting of sapstain and sooty mould.

3. The method of claim 1 wherein the controlled fungi are a mixture of Basidiomycetes and at least one member selected from the group consisting of sapstain and sooty mould.

4. The method of claim 1 wherein the controlled fungus is at least one member selected from the group consisting of *Corioluts versicolor, Poria placenta, Lentinus lepideus, Trametes versicolor, Serpula lacrymans, Coniophora puteania,* and *Gloeophyllum trabetum.*

5. The method of claim 2 wherein the fungicidal composition further comprises at least one additional wood fungicide.

6. The method of claim 5 wherein the additional wood fungicide is selected from the group consisting of fluquinconazole, tebuconazole, dichlone, carbendazim, prochloraz, sipconazole, and cyproconazole.

7. The method of claim 1 wherein the compound is of the structural formula:

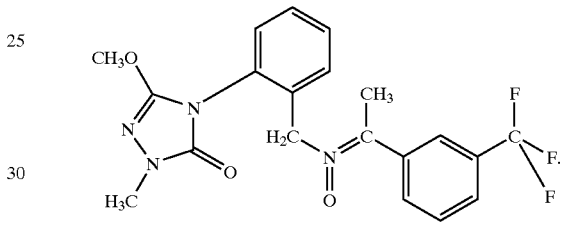

8. The method of claim 7 wherein the controlled fungus is at least one member selected from the group consisting of sapstain and sooty mould.

9. The method of claim 7 wherein the controlled fungi are a mixture of Basidiomycetes and at least one member selected from the group consisting of sapstain and sooty mould.

10. The method of claim 7 wherein the controlled fungus is at least one member selected from the group consisting of *Coriolus versicolor, Poria placenta, Lentinus lepideus, Trametes versicolor, Serpula lacrymans, Coniophora puteana,* and *Gloeophyllum trabeum.*

11. The method of claim 8, wherein the fungicidal composition further comprises at least one additional wood fungicide.

12. The method of claim 11, wherein the additional wood fungicide is selected from the group consisting of fluquinconazole, tebuconazole, dichlone, carbendazim, prochloraz, sipconazole, and cyproconazole.

* * * * *